(12) United States Patent
Atwood et al.

(10) Patent No.: US 7,217,846 B2
(45) Date of Patent: May 15, 2007

(54) CALIXARENE-BASED GUEST-HOST ASSEMBLIES FOR GUEST STORAGE AND TRANSFER

(76) Inventors: Jerry L. Atwood, 5704 Short Line Dr., Columbia, MO (US) 65203; Leonard J. Barbour, 2240 E. Bluebird La., Columbia, MO (US) 65201; Agoston Jerga, 1700 Forum Blvd., #2908, Columbia, MO (US) 65203

( * ) Notice: Subject to any disclaimer, the term of this patent is extended or adjusted under 35 U.S.C. 154(b) by 282 days.

(21) Appl. No.: 10/286,179

(22) Filed: Oct. 31, 2002

(65) Prior Publication Data

US 2004/0087666 A1 May 6, 2004

(51) Int. Cl.
*C07C 39/12* (2006.01)
(52) U.S. Cl. .................................................. 568/719
(58) Field of Classification Search ................ 568/719
See application file for complete search history.

(56) References Cited

U.S. PATENT DOCUMENTS

| 4,090,129 | A | 5/1978 | Gear |
| 4,192,869 | A | 3/1980 | Nicolau et al. |
| 4,438,259 | A | 3/1984 | Meyer et al. |
| 5,711,927 | A | 1/1998 | Atwood et al. |
| 6,432,918 | B1 | 8/2002 | Winslow |

OTHER PUBLICATIONS

"Calixarene cyrstals as new absorption agents for the purification of hydrogen", Chemie.De Information Service, http://www.chemie.de/news/e/37747/ (May 24, 2004).*
Giovanni Dario Andreetti☐☐Crystal and Molecular structure of Cyclo{quater[(5-t-butyl-2-hydroxy-1,3-phenylene)methylene]}Toluene (1:1) Clathrate☐☐J.C.S.Chem. Comm., 1979, 1005-1007.*
Eric B.Brouwer, Konstantin A. Udachin, Gary D. Enright, Christopher I. Ratcliffe and John A. Ripmeester☐☐Chem. Commun., 1998 p. 587-588.*
Self-Inclusion and paraffin intercalation of the p-tert-butylcalix[4]arene host:a neutral organic clay mimc☐☐Eric B.Brouwer, Kostantin A.Udachin, Gary D. Enright, John A. Ripmeester, Kristopher J.Ooms and Peter A.Halchuk☐☐Chem. Commun., 2001, 565-566.*
A.W. Coleman et al., Electron Transfer and Charge Transfer: Twin Themes in Unifying the Mechanisms of Organic and Organometallic Reactions, Agnew. Chem. Int. Ed. Engl., 1988, pp. A-205, 1361-1362, vol. 27, No. 10, A Journal of the Gesellschaft Deutscher Chemiker, Germany.
E.B. Brouwer et al., Self-inclusion and Paraffin Intercalation of the p-tert-butylcalix[4] arene host: A Neutral Organic Clay Mimic, Chem. Commun., 2001, pp. 565-566, Royal Society of Chemistry, UK.

* cited by examiner

*Primary Examiner*—Samuel A Barts
*Assistant Examiner*—Lalitha Nagubandi
(74) *Attorney, Agent, or Firm*—William D. Jackson

(57) ABSTRACT

A guest host assembly comprising a host assembly formed of calixarene molecules and a guest component located within the host assembly. A crystallographic assembly of layers of the calixarene molecules and stacked along the crystallographic c axis of the assembly in a repeating configuration associated together predominantly by van der Waal forces. The guest component is transferable through the host assembly in a direction normal to the stacked layers. The calixarene molecules are configured in bilayers of adjacent layers along the c axis. The bilayers are shifted along the a or b axis so the assembly, relative to a corresponding assembly of the calixarene molecules without the inclusion of the guest component is shifted. The calixarene are calix(N)arenes in which N is an integer within the range of 4–8. The calixarene molecules are distally substituted with a substituent such as methyl, ethyl, propyl, butyl amyl or phenyl groups.

32 Claims, 1 Drawing Sheet

CALIXARENE-BASED GUEST-HOST ASSEMBLIES FOR GUEST STORAGE AND TRANSFER

FIELD OF THE INVENTION

This invention relates to layered host assemblies formed of calixarene molecules and molecules of guest species and the preparation of such assemblies and their use in transmitting and separating species of guest components.

BACKGROUND OF THE INVENTION

Calixarenes are complex cyclic compounds that can undergo self-assembly to form guest host complexes. In such complexes, a guest component can be incorporated within the calixarene-based structure which encapsulates the guest material. The simplest calixarene is calix(4)arene in which four phenyl groups are linked together in a cyclic array by methylene bridges which are proximal to the OH groups of the phenols. Stress induced within the calixarene molecules result in indented or bowl-shaped, and the calixarenes can be assembled to form a supramolecular structures.

The assembly of organic molecular crystals such as those based on supramolecular assemblies of calixarene molecules is primarily controlled by a variety of intermolecular interactions which, in unison, immobilize the building blocks to form stable arrays. When these materials are heated beyond their melting or sublimation points, the cohesive forces are overcome, resulting in increased mobility and disorganization of the molecules. The molecules of a solid can also be mobilized by processes such as dissolution and solid-solid phase changes. The latter can occur as a result of physical stimuli (e.g. temperature, pressure, radiation) or the gain or loss of ancillary molecular components. While inclusion of either a liquid or gaseous guest by a solid matrix is a well-known phenomenon, the mechanisms of such processes are not well defined. In organic solid state guest host assemblies where transport of the guest through the host, and subsequent complexation, usually involves concomitant reorganization of the host lattice (7). Guest-induced lattice rearrangement often result in severe fracturing of single crystals into polycrystalline material. When fracturing does not occur, alternative mechanisms postulate the presence of stable channels through which mobile guest molecules diffuse until a thermodynamically stable host-guest structure is achieved.

SUMMARY OF THE INVENTION

In accordance with the present invention, there is provided a guest host assembly comprising a host assembly formed of calixarene molecules and a guest component located within the host assembly. The calixarene molecules are formed in a crystallographic assembly of layers of the calixarene molecules stacked along the crystallographic c axis of the assembly in a repeating configuration associated together predominantly by van der Waal forces. The crystallographic assembly is stable at a temperature of at least 40° C. The guest component within the host assembly is transferable through the host assembly in a direction normal to the stacked layers. The calixarene molecules are configured in bilayers of adjacent layers along the c axis of the assembly. If the bilayers are shifted in the process of guest inclusion, the bilayers are shifted along the a or b access in a specific embodiment of the invention.

The calixarene molecules may be characterized as calix(N)arenes in which N is an integer within the range of 4–8. Thus the calixarenes ranging from calix(4)arene to calix(8)arene can be employed in carrying out the invention. The calixarene molecules are distally substituted with a substituent selected from the group consisting of methyl, ethyl, propyl, butyl amyl or phenyl groups. Preferably, the calixarene molecules are substituted at the para position, and a preferred calixarene for use in carrying out the invention is para tertiary butyl calix(4)arene.

In a further aspect of the invention there is provided a process for the inclusion of a fluid guest component in a guest-host assembly. In carrying out the process, there is provided a layered host assembly of calixarene molecules in a crystallographic assembly with layers of the molecules stacked along the c axis of the assembly in repeating configuration with association due predominantly to van der Waals' forces. The layers form a repeating configuration of bilayers of adjacent layers along the c axis. A guest component is incorporated into the host assembly to form a guest host assembly in which the inclusion of the guest component provides for a shirt of the bilayers along the a or b axis of the assembly [to form repeating layers of the calixarene molecules and provide a crystallographic assembly, having a unit axis along the c axis which is less than the crystallographic c axis of the assembly prior to the inclusion of the guest compliment.

In yet a further embodiment of the invention there is provided a process for the purification of a fluid guest component found in an ambient zone containing the guest component in admixture with at least one contaminant. A layered host assembly formed of layers of calixarene molecules is formed as described above. The layered host assembly is interposed between the ambient zone and a purification zone in an orientation in which the c axis of the crystallographic assembly is parallel in orientation between the ambient zone and the purification zone to provide that the a or b axis of the crystallographic assembly extends between the ambient zone and the purification zone. The guest component is transferred through the crystallographic assembly along the a or b axis of the crystallographic assembly to the purification zone.

DETAILED DESCRIPTION OF THE INVENTION

Figures 1A, 1B:
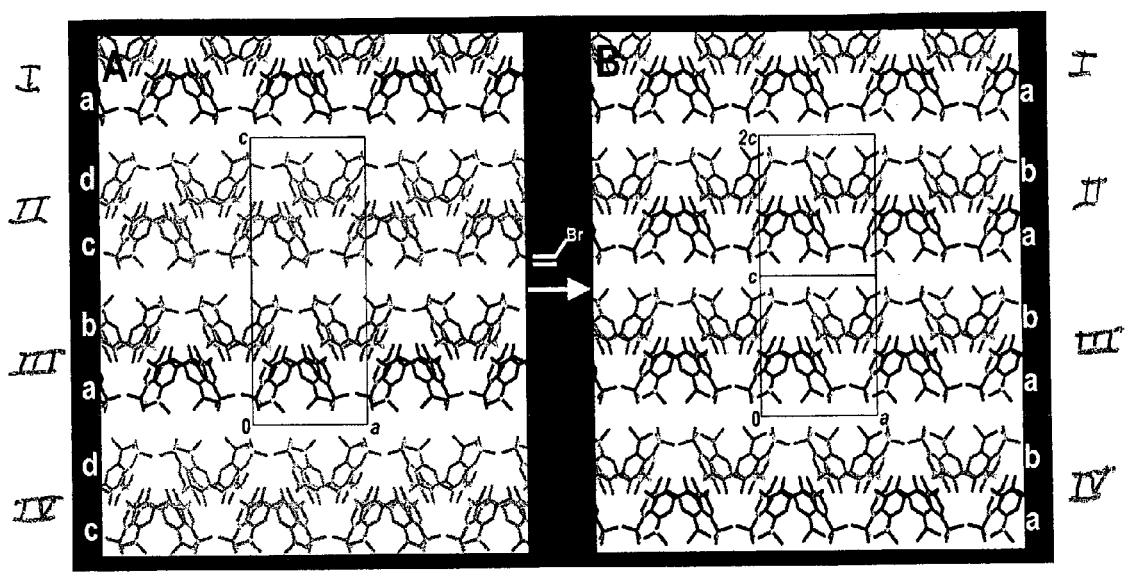
FIG. 1A is a schematic side elevational view, showing the packing of layers of calixarene molecules in a crystalline structure without the inclusion of a guest component.
FIG. 1B is a schematic site elevational view showing the packing position of calixarene layers after the inclusion of a guest component.

The present invention involves an organic supramolecular crystallographic framework that is stabilized predominately by van der Waals interactions and which is selectively permeable to fluid (liquid or gas) guest components. The supramolecular assemblies involved in the present invention are based upon assemblies of calixarenes or derivatives of calixarenes. The preferred application of the invention involves the use of para-substituted calix[4]arenes, such as para-tertiarybutyl calix[4]arene. However, other substituted calixarenes, such as distally substituted calix(5)arene, calix[6]arene and calix[8]arene, can be employed in carrying out the invention. Derivatives of such calixarenes can be employed to achieve the crystallographic assemblies involved in the present invention. However, contrary to functionalized calixarenes, such as resorcinarenes, the calixarenes employed in the present invention are assembled predominantly by van der Waals forces as opposed to strong chemical bonding, such as may be achieved through the use of functional substituents on the aromatic nuclei. The invention will be described in detail with regard to the use of para-tertiarybutyl calix[4]arene to form stacked layered calixarene assemblies for the transference of low molecular weight guest moieties.

The calixarenes comprise an extensively studied class of macrocyclic polyphenolic compounds that are usually strongly associated with host/guest inclusion chemistry. The simplest representative of this family of compounds is calix[4]arene, which forms from four methylene-bridged phenyl groups, as indicated by the following structural formula:

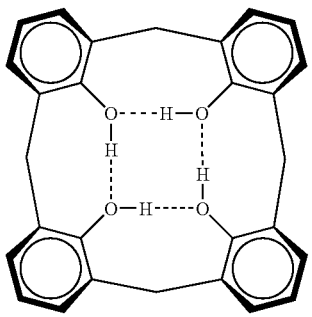

(1)

Calix[4]arene provides a bowl-shaped molecule with a shallow cleft and a rigid cone conformation which is stabilized by a cyclic array of hydrogen bonds between adjacent phenolic OH groups at the lower rim. As indicated by the experimental work described below respecting calix[4]arene, its crystalline inclusion compounds exhibit particularly unusual structural characteristics, in addition to good thermal stability.

While the calixarene compounds employed in carrying out the present invention will normally be fully aromatized, as indicated by the Structure (1), one or more of the aryl groups may be hydrogenated. For example, a calixarene suitable for use in carrying out the present invention would include cyclohexylcalixarene in which one aromatic group has been hydrogenated to form a cyclohexyl group, as indicated by the following structural formula.

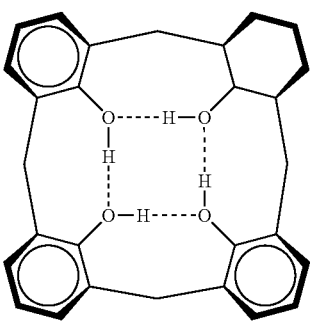

(2)

In addition, the bridge groups formed by the methylene bridges can be replaced by other bridged structures which are sterically similar to the methylene bridges. For example, sulfur bridges can be provided in lieu of the carbon bridges, as indicated by the thiocalixarene shown by the following structural formula.

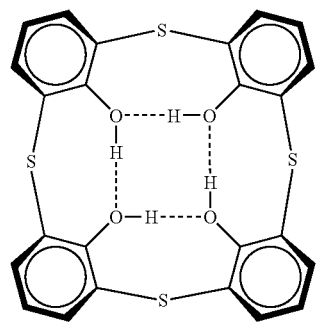

(3)

Other suitable bridging agents would include silanyl groups in which the methylene groups are replaced with silanyl, —$SiH_2$—. As will be recognized by those skilled in the art, such calixarene derivatives bear a very close stearic configuration to the normally encountered calixarenes. Such compounds may also incorporate hydrogenated aromatic groups, similarly as shown by the cyclohexyl-calix[4]arene of Formula (2).

The embodiment of the invention carried out involving calix[4]arene will be described with reference to the fully aromatized methylene-bridged calix[4]arene depicted by Formula (1). However, it will be recognized that such description is also applicable to the use of calix[4]arene involving hydrogenated aryl groups, as depicted by Formula (2), or by calix[4]arenes formed with bridges other than methylene bridges, such as depicted by Formula (3).

The calixarenes employed in the present invention are substituted on the ring structure at a distal position relative to the OH group at the lower rim of the calixarene molecule. Preferably, the calixarenes are parasubstituted, that is, substituted at the directly distal position as indicated by the following structural formula.

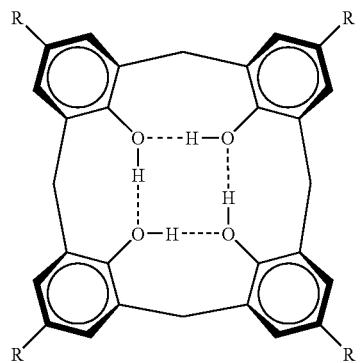

(4)

In formula (4), R is a substituent, preferably a somewhat bulky substituent, which can function as described later to sterically interact within the calixarene cavity of an adjacent calixarene molecule. Preferably, the substituent is a tertiary butyl group so that the calixarene is shown by the following structural formula.

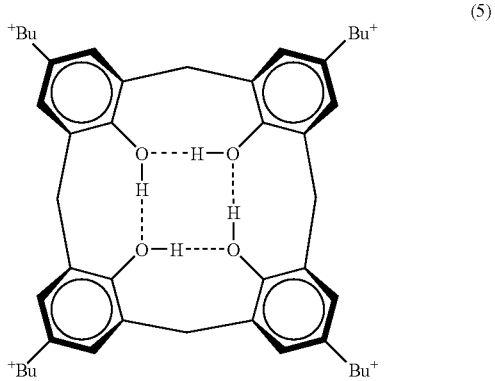

(5)

Depending upon the guest component involved and the desired transmissibility of the guest component through the calixarene assembly the substituents may take the form of other substituents such as isopropyl groups or isoamyl groups?

While calix(4)arene will normally be employed in carrying out the present invention, as noted previously, substituted derivatives of higher molecular weight calixarenes may also be employed. These higher molecular weight calixarenes may be characterized as calix(N)arenes wherein N is within the range of 4–8. Preferably, the calixarene will normally take the form of a calix(4)arene or a calix(5)arene.

The nature of the distal substituents on the calixarene molecules may also vary. While the substituent is preferably isopropyl, tertiarybutyl an isoamyl group such as an isopentyl or a neopentyl, other substituent groups can include methyl groups, ethyl groups or aromatic groups such as phenyl groups or cycloalkyl groups such as cyclohexyl groups. Bearing in mind that the stacked layers of calixarene employed in the present invention involve stearic interaction between the substituent groups of one calixarene molecule with the "bowl" of an adjacent calixarene molecule it will be recognized that the substituent groups may be configured depending upon the molecular weight of the calixarene base molecule. Thus, lower molecular weight constituent groups may be more appropriate where the calixarene is a calix(4) arene or a calix(5)arene whereas higher molecular weight substituent groups such as isoamyl groups or phenyl groups may be appropriate where a higher molecular weight calixarene such as calix(6)arene or a calix(8)arene is involved.

The present invention involves the incorporation of guest species in a structure of a purely organic solid that does not contain channels, but nevertheless facilitates the diffusion of guest species through its lattice. Uptake of the guest involves a single-crystal-to-single-crystal phase transformation with considerable displacement of the host molecules in two dimensions to give a non-porous inclusion complex. Experimental work respecting the invention shows that the organic solid state is significantly more dynamic than would be expected, and that the usually immobile molecules can be reorganized in an orderly fashion by weak dispersive forces.

In describing the crystallographic assemblies referred to herein, conventional crystal lattice nomenclature is employed. Thus, crystallographic structures are characterized in terms of a vertical c axis and two horizontal a and b axes at an orientation of 90° to one another.

Crystals of p-Bu$^t$-calix[4]arene were prepared by sublimation of p-Bu$^t$-calix[4]arene at 280° C. under a reduced pressure of 1–10 torr. Single crystal x-ray analysis of the resulting sublimed unsolvated form of p-Bu$^t$-calix[4]arene, reveals that the calixarene molecules arrange themselves into a bilayer packing motif of a type conforming to that described in A. W. Coleman et al., Angew. Chem. Int. Ed. Engl. 27, 1361 (1988). Pairs of offset facing calixarene molecules are characterized as dimers that form skewed capsules, each with an estimated free volume of 235 Å$^3$. As a result of these relatively large lattice voids, the sublimed, unsolvated p-Bu$^t$-calix[4]arene has a rather low packing efficiency (p.e.) of 0.59. In comparison, it should be noted that a polymorphic form of p-Bu$^t$-calix[4]arene grown from a tetradecane solution, has recently been described in E. B. Brouwer et al., Chem. Commun. 565 (2001). The structure of unsolvated p-Bu$^t$-calix[4]arene crystallized from a tetradecane solution consists of a well-packed (p.e.=0.67) arrangement of calixarene dimers, where each of the two facing molecules inserts one of its Bu$^t$ groups deep into it's neighbor's cavity. The x-ray powder defraction pattern of the p-tertiary Bu$^t$-calix[4]arene in polymorphic Form 1 (as crystallized from a tetradecane solution) and Form 2 (as sublimed, unsolvated) as calculated from a single crystal x-ray defraction data are set forth in Tables 1 and 2, respectively. Tables 1 and 2 set forth the value of a two-theta (theta being the bragg angle) with the corresponding interplanar d spacings in angstroms, along with the relative intensities of the x-ray reflections observed at the indicated d spacings.

TABLE 1 p-tert-butylcalix[4]arene, polymorph Form 1,
calculated from single crystal X-ray diffraction data

| 2θ | d spacing | relative intensity |
|---|---|---|
| 7.52 | 11.75 | 100 |
| 9.81 | 9.01 | 21 |
| 10.23 | 8.64 | 63 |
| 11.49 | 7.70 | 56 |
| 14.12 | 6.27 | 44 |
| 14.20 | 6.23 | 22 |
| 15.20 | 5.82 | 24 |
| 16.11 | 5.50 | 28 |
| 16.42 | 5.39 | 18 |
| 16.54 | 5.36 | 42 |
| 17.55 | 5.05 | 58 |
| 18.79 | 4.72 | 27 |
| 19.42 | 4.57 | 18 |
| 19.69 | 4.50 | 26 |
| 20.07 | 4.42 | 43 |
| 20.10 | 4.41 | 27 |
| 21.47 | 4.14 | 20 |
| 21.56 | 4.12 | 18 |
| 21.91 | 4.05 | 28 |
| 23.78 | 3.74 | 23 |

TABLE 2 p-tert-butylcalix[4]arene, polymorph Form 2,
from powder X-ray diffraction data

| 2θ | d spacing | relative intensity |
|---|---|---|
| 6.48 | 13.62 | 100 |
| 13.78 | 6.42 | 8 |
| 16.70 | 5.31 | 6 |
| 16.78 | 5.28 | 6 |
| 20.02 | 4.43 | 14 |
| 20.44 | 4.34 | 6 |

*2θ values are +/− 0.10°

Purely organic solid-state frameworks rarely contain substantial lattice voids such as those observed in sublimed, unsolvated p-Bu$^t$-calix[4]arene. Indeed, the molecular arrangement in the unsolvated p-Bu$^t$-calix[4]arene crystallized from tetradecane solution clearly demonstrates that p-Bu$^t$-calix[4]arene is capable of packing quite efficiently in its pure form. The striking disparity in packing efficiency between sublimed, unsolvated p-Bu$^t$-calix[4]arene, Form 2 (Table 2), and the unsolvated p-Bu$^t$-calix[4]arene as crystallized from a tetradecane solution, Form 1 (Table 1), supports the view that sublimed, unsolvated p-Bu$^t$-calix[4]arene should readily undergo guest inclusion reactions in order to gain further thermodynamic stability.

A single crystal of sublimed, unsolvated p-Bu$^t$-calix[4]arene was soaked in vinyl bromide at −5° C. for 15 minutes. X-ray diffraction analysis of the still intact crystal confirmed that a single-crystal-to-single-crystal phase transformation had occurred, resulting in a 1:1 host:guest complex of p-Bu$^t$-calix[4]arene and vinyl bromide. An inspection of the sublimed, unsolvated p-Bu$^t$-calix[4]arene and the 1:1 complex of p-Bu$^t$-calix[4]arene and vinyl bromide shows clearly that neither structure is porous. Nevertheless, transport of vinyl bromide through the lattice is readily facilitated as a homogeneous process as evidenced by the single-crystal-to-single-crystal transformation which takes place over a period of only 15 minutes.

The sublimed, unsolvated p-Bu$^t$-calix[4]arene form of p-Bu$^t$-calix[4]arene crystallizes in the monoclinic system (space group P112$_1$/n) and the calixarene molecules are stacked in an up-down fashion in discrete layers designated as a, b, c and d along the crystallographic c axis (FIG. 1A). Bilayers ab and cd each comprise closely-packed calixarene molecules with a stacking interval of 13.12 Å. Both surfaces of each bilayer are lined with Bu$^t$ groups which form bulky protrusions separated by small crevices. Adjacent bilayers are only slightly interdigitated: three Bu$^t$ groups of each calixarene moiety nestle into the crevices of an adjacent bilayer surface, while the remaining Bu$^t$ group is positioned in a gap between several neighboring molecules. Owing to a less constricted environment, the latter is disordered over two positions.

A preferred application of the present invention is in the selective entrainment of low molecular weight hydrocarbons, specifically $C_1$–$C_4$ aliphatic compounds in the guest host complex. Thus, the guest component can take the form of a methane or a $C_2$–$C_4$ aliphatic compound which is either saturated or unsaturated. Such compounds include, in addition to methane, ethane, ethylene, propane, propylene, butane and butylene.

The host assembly can be configured to separate the components in an ethylene ethane mixture to arrive at pure ethylene and ethane components. Thus, guest-host assemblies which can be provided for in the course of the present invention, include assembles incorporating crystallographic structures of p-Bu$^t$-calix[4]arene as the host component with methane, ethylene or ethane as the guest component. Similar assemblies can be formulated in which propylene, propane, butylene or butane is the guest component.

FIG. 1 illustrates the difference in packing between the crystal structure of the sublimed unsolvated p-butyl calix(4)arene (FIG. 1A), and the corresponding structure of the 1:1 complex of p-Bu$^t$-calix[4]arene and vinyl bromide (FIG. 1B). In FIG. 1 the views of the layers of calixarene are shown along [010]. The c axis of the crystal structure is the vertical axis, the a axis is in the plane of the paper and the b axis, of course, is in a plane projecting out of the paper. In FIG. 1A, the calixarene molecules are shown as packed as repeating layers designated by a, b, c, and d. Two distinct bilayers formed of layers a and b and c and d can be distinguished. Thus, as illustrated in FIG. 1A from top to bottom, there is illustrated a first bilayer I, formed of layers b and a, a second bilayer II formed of layers d and c, a third bilayer, III, formed of layers b and a, and a fourth bilayer, IV, formed of layers d and c. Upon inclusion of vinyl bromide by the calixarene to form the 1:1 complex of the calixarene and vinyl bromide, the bilayers I and II and III and IV have shifted relative to one another. As a consequence of this shift, the space group symmetry of the host lattice is increased from P112$_1$/n (pseudo tetragonal, but monoclinic, a=12.675(5), b=12.608(5), c=25.687(10) Å, γ=90.273(8)°) to P4/n (tetragonal, a=b=12.801(3), c=12.853(6) Å), with the calixarene molecules now packing as repeating layers of type ab/ab. The c unit cell axis of the structure of FIG. 1B is approximately half that of FIG. 1A.

Upon incorporation of vinyl bromide into the calixarene lattice, the bilayer packing motif of sublimed, unsolvated p-Bu$^t$-calix[4]arene is maintained in the resulting phase of the complex of p-Bu$^t$-calix[4]arene and vinyl bromide. While the relative positions of the calixarene molecules within each bilayer remain essentially unchanged, adjacent bilayers are translated along approximately [210] by 5.9 Å with respect to one another after guest inclusion. Furthermore, the calixarene molecules of adjacent bilayers maintain their relative orientations within the crystal. The lateral translation of the bilayers results in an overall increase in the crystallographic point group symmetry from 2/m in sublimed, unsolvated p-Bu$^t$-calix[4]arene to 4/m in the 1:1 complex of p-Bu$^t$-calix[4]arene and vinyl bromide as the p-Bu$^t$-calix[4]arene, originally stacked as ab/cd bilayers, reorganizes to form ab/ab bilayers. Consequently, the c unit cell axis of 1:1 complex of p-Bu$^t$-calix[4]arene and vinyl bromide is approximately half that of sublimed, unsolvated p-Bu$^t$-calix[4]arene. In the 1:1 complex of p-Bu$^t$-calix[4]arene and vinyl bromide, each host molecule is associated with one molecule of vinyl bromide and the overall packing efficiency, p.e., is 0.64. The vinyl bromide molecule inserts its =$C_2H_4$ moiety deeply into the calixarene cavity while the bromine atom is positioned between the four Bu$^t$ groups. As observed in sublimed, unsolvated p-Bu$^t$-calix[4]arene, the Bu$^t$ groups lining the surfaces of the bilayers nestle into the crevices of adjacent bilayers. The spacing of the bilayers in the sublimed, unsolvated p-Bu$^t$-calix[4]arene and the complex of p-Bu$^t$-calix[4]arene and vinyl bromide differ by only 0.01 Å, indicating that, upon guest uptake, the bulk crystal expands by only 0.08% along [001]. A comparison of the unit cell dimensions shows that the crystal volume increases by 2.6%. Although the ~6 Å shift in the bilayers relative to one another represents a significant displacement on the molecular scale, this movement of the molecules is not compounded throughout the crystal, i.e. the bilayers can conceivably shift in opposing directions parallel to (110). These net translations indicate that, on the macroscopic scale, the crystal experiences little physical stress during the phase transition process, thus offering a plausible explanation for the retention of its single-crystal character.

To investigate the mechanism of the phase transition, experiments were carried out with a series of vinyl bromide treatments using a crystal p-Bu$^t$-calix[4]arene of approximate dimensions 0.4×0.4×0.2 mm$^3$. After exposure to vinyl bromide for 5 minutes, the crystal retained the guest-free monoclinic structure described above. However, a further 5-minute exposure resulted in a single crystal containing both phases of the sublimed, unsolvated p-Bu$^t$-calix[4]arene and the 1:1 complex of p-Bu$^t$-calix[4]arene and vinyl bromide. Therefore, after a total of ten minutes of exposure to vinyl bromide, the crystal is trapped in an intermediate stage in the single-crystal-to-single-crystal transformation. Significantly, upon exposure to the atmosphere at ambient temperature for 18 hours, with no additional vinyl bromide present, this intermediate crystal completely transformed into the tetragonal phase of the 1:1 complex of p-Bu$^t$-calix[4]arene and vinyl bromide. Structure analysis after this 18-hour period shows 60% occupancy of vinyl bromide in the guest pockets. Thus, in the absence of vinyl bromide from the surface of the crystal, the phase transformation continues until the tetragonal structure or the 1:1 complex of p-Bu$^t$-calix[4]arene and vinyl bromide is formed. This is consistent with the postulate that, once the phase transformation has been initiated, the host lattice seeks out the thermodynamically stable commensurate structure of the 1:1 complex of p-Bu$^t$-calix[4]arene and vinyl bromide.

A survey of the Cambridge Crystallographic Database reveals that the host lattice of the 1:1 complex of p-Bu$^t$-calix[4]arene and vinyl bromide is isomorphous with that of a previously reported 1:1 adduct of p-Bu$^t$-calix[4]arene with toluene (P4/n, a=b=12.604, c=13.871 Å). All attempts to infuse toluene into sublimed, unsolvated p-Bu$^t$-calix[4]arene in the manner described above resulted in dissolution of the crystal. When crystals of a 1:1 complex of p-Bu$^t$-calix[4]arene and toluene were subjected to thermogravimetric analysis, two separate weight-loss events were observed with onset temperatures of 115 and 160° C. respectively, each accounting for half of the total amount of toluene guest. In a further experiment, after heating a crystal of a 1:1 complex of p-Bu$^t$-calix[4]arene and toluene at 115° C. for 25 minutes, it was found to still be suitable for single-crystal x-ray diffraction analysis. As inferred from the thermal studies, the resulting structure proved to be that of the 2:1 host:guest adduct of p-Bu$^t$-calix[4]arene with toluene (P4/nnc, a=b=12.911, c=25.061 Å). Detailed comparison of the host lattices of the 1:1 complex of p-Bu$^t$-calix[4]arene and toluene and the 2:1 complex of p-Bu$^t$-calix[4]arene and toluene reveals that, with respect to the transition from sublimed, unsolvated p-Bu$^t$-calix[4]arene to 1:1 complex of p-Bu$^t$-calix[4]arene and vinyl bromide, an even more dramatic shift of the bilayers occurs during the single-crystal-to-single-crystal transformation when half of the toluene is removed from the 1:1 complex of p-Bu$^t$-calix[4]arene and toluene. Not only do adjacent ab/ab bilayers in 1:1 complex of p-Bu$^t$-calix[4]arene and toluene slide along one another by ~9 Å to once again yield a motif of type ab/cd in the 2:1 complex of p-Bu$^t$-calix[4]arene and toluene, but the calixarene molecules are rotated by 38° relative to those of an adjacent bilayer. It should be noted that neither the 1:1 complex of p-Bu$^t$-calix[4]arene and toluene nor the 2:1 complex of p-Bu$^t$-calix[4]arene and toluene is porous.

The foregoing work indicates that p-Bu$^t$-calix[4]arene undergoes several different, but related, phase transitions upon uptake and release of a guest component. These transitions occur without destruction of the single crystal character of the lattice on a macroscopic scale as would result from dissolution and regrowth of the crystalline material. This supports the following as a plausible mechanism for guest transport through the lattice, and concomitant reorganization of the host molecules. These processes can be rationalized by considering the initial and final structures, as well as incremental stages along the net vector representing the overall shift of neighboring bilayers with respect to one another. Using this simplistic approach, it is not possible to identify any intermediate quasicrystalline states with the required porosity to allow unconstrained guest diffusion through the crystal. This supports the conclusion that the guest sport mechanism involves a cooperative process whereby neighboring host molecules transfer guest molecules to one another without ever forming continuous channels that traverse the structure, i.e. the mechanism must involve the active passage of delocalized guest-pockets through the lattice. This mechanism is also operative in the formation of the methane para tertiary butyl calix[4]arene guest host compound and the hydrogen para tertiary butyl calix[4]arene guest host compound.

Clearly the host molecules can be immobilized to yield highly stable structures of either the pure material or, in the presence of a suitable guest, an inclusion compound. Equally clearly, the host molecules can be mobilized in response to relatively weak van der Waals interactions with small guest species such as vinyl bromide or toluene. Indeed, during a phase transition, the dynamics of the host lattice must occur as a highly synchronized process whereby neighboring host molecules at the advancing phase boundary cooperate with one another, not only to relay the guest through the lattice, but also to maintain continuity of the material such that the crystal does not fracture. Therefore, the implication of this observation is that, in the organic solid state, relatively large molecules can demonstrate a surprising degree of mobility involving extensive cooperation between one another.

Having described specific embodiments of the present invention, it will be understood that thereof may be suggested to those skilled in the art, and it is intended to cover all such modifications as fall within the scope of the appended claims.

The invention claimed is:

1. A composition of matter comprising a guest-host assembly having:
    (a) a host assembly formed of calixarene molecules in a crystallographic assembly of layers of said calixarene molecules stacked along the c axis of said assembly in a repeating configuration associated together predominantly by van der Waals forces, said crystallographic assembly being stable at a temperature of at least 40° C.;
    (b) a guest component located within said host assembly and transferable through said host assembly in a direction normal to said stacked layers; and
    (c) said calixarene molecules being configured in bilayers of adjacent layers of said calixarene molecules along the c axis of said assembly, said bilayers being shifted along the a or b axis of said assembly relative to a corresponding assembly of said calixarene molecules without the inclusion of said guest component to provide a unit cell c axis which is less than the unit cell c axis of said corresponding assembly of said calixarene molecules.

2. The composition of claim 1 wherein said calixarene molecules are calix(N)arenes wherein N is an integer within the range of 4–8.

3. The composition of claim 2 wherein said calixarene molecules are distally substituted with a substituent selected from the group consisting of a methyl group, an ethyl group, a propyl group, a butyl group, an amyl group and a phenyl group.

4. The composition of claim 3 wherein said calixarene molecules are substituted at the para position.

5. The composition of claim 2 wherein said calixarene molecules are calix[4]arene or calix[5]arene.

6. The composition of claim 1 wherein said calixarene is a para R calix[4]arene or calix[5]arene wherein R is an isopropyl group or a tertiary butyl group.

7. The composition of claim 1 wherein said calixarene molecules comprise calix[4]arene, cyclohexyl-calix[4]arene, or thiocalix[4]arene substituted at the para position with an isopropyl group or a tertiary butyl group.

8. The composition of claim 1 wherein said calixarene is para tert butyl calix[4]arene.

9. In a process for the inclusion of a fluid component in a guest host assembly comprising:
  (a) providing a layered host assembly formed of calixarene molecules in a crystallographic assembly of layers of said calixarene molecules stacked along the c axis of said assembly in a repeating configuration associated together predominantly by van der Waals forces and a repeating configuration of bilayers formed of adjacent layers of said calixarene molecules, said crystallographic assembly being stable at a temperature of at least 40° C.;
  (b) incorporating a guest component in said host assembly to form a guest host assembly in which the inclusion of said guest component provides for a shift of said bilayers along the a or b axes of said assembly to form repeating layers of said calixarene molecules.

10. The process of claim 9 wherein said calixarene molecules are calix[N]arenes wherein N is an integer within the range of 4–8.

11. The process of claim 10 wherein said calixarene molecules are distally substituted with a substituent selected from the group consisting of a methyl group, an ethyl group, a propyl group, a butyl group, an amyl group and a phenyl group.

12. The process of claim 11 wherein said calixarene molecules are substituted at the para position.

13. The process of claim 9 wherein said calixarene molecules are calix[4]arene or calix[5]arene.

14. The process of claim 9 wherein said calixarene is a para R calix[4]arene or calix[5]arene wherein R is an isopropyl group or a tertiary butyl group.

15. In a process for the purification of a fluid guest component in an ambient zone containing said guest component in admixture with at least one contaminant:
  (a) providing a layered host assembly formed of layers of calixarene molecules in a crystallographic assembly of layers of said calixarene molecules in a repeating configuration associated together predominantly by van der Waals forces, said crystallographic assembly being stable at a temperature of at least 40° C.;
  (b) interposing said layered host assembly between said ambient zone and a purification zone in an orientation in which the c axis if said crystallographic assembly is parallel to said ambient zone and said purification zone, with the a or b axis of said crystallographic assembly extending between said ambient zone and said purification zone; and
  (c) transferring said guest component from said ambient zone to said purification zone through said crystallographic assembly and along the a or b axis of said crystallographic assembly.

16. The process of claim 15 wherein said calixarene molecules are calix[4]arene or calix[5]arene.

17. The process of claim 15 wherein said calixarene is a para R calix[4]arene wherein R is an isopropyl group or a tertiary butyl group.

18. A process for transferring a fluid guest component through a solid state host comprising:
  (a) providing a layered host assembly formed of calixarene molecules in a crystallographic assembly of layers of said calixarene molecules stacked along the c axis of said assembly in a repeating configuration associated together predominantly by van der Waals forces and providing a repeating configuration formed of bilayers of adjacent layers of said calixarene molecules, said crystallographic assembly being stable at a temperature of at least 40° C.;
  (b) introducing a fluid guest component into the edge of said host assembly to cause a flow of the molecules of said guest component along said layers to provide for an attendant shift of said bilayers along the a or b axes of said assembly to form repeating bilayers of said calixarene molecules;
  (c) continuing the introduction of said guest component into the edge of said crystallographic assembly with the cooperative transfer of the molecules of said guest component between adjacent calixarene molecules along the a or b axes of said crystallographic assembly; and
  (d) withdrawing said gas component from the said crystallographic assembly and at edge of said assembly opposing said first recited edge.

19. The process of claim 18 wherein said calixarene molecules are calix[N]arenes wherein N is an integer within the range of 4–8.

20. The process of claim 19 wherein said calixarene molecules are distally substituted with a substituent selected from the group consisting of a methyl group, an ethyl group, a propyl group, a butyl group, an amyl group and a phenyl group.

21. The process of claim 19 wherein said calixarene molecules are calix[4]arene or calix[5]arene.

22. The process of claim 18 wherein said calixarene is a para R calix[4]arene or calix[5]arene wherein R is an isopropyl group or a tertiary butyl group.

23. The process of claim 18 wherein said calixarene is para tert butyl calix[4]arene.

24. A guest host assembly comprising:
  (a) a host assembly formed of molecules of para tertiary butyl calix[4]arene and a crystallographic assembly of said molecules stacked along the c axis of said crystallographic assembly in a repeating configuration associated together predominantly by van der Waals forces;
  (b) A guest component comprising a $C_1$–$C_4$ aliphatic hydrocarbon and transferable through said host assembly in a direction normal to the c axis of said crystallographic assembly; and
  (c) said calixarene molecules being configured in bilayers of adjacent layers of said calixarene molecules along the c axis of said assembly, said bilayers being shifted along the a or b axis of said assembly relative to a corresponding assembly of said calixarene molecules without the inclusion of said guest component to provide a unit cell c axis which is less than the unit cell c axis of said corresponding assembly of said calixarene molecules.

25. The composition of claim 24 wherein said guest component is selected from a group consisting of methane, ethylene and ethane.

26. A composition of matter comprising polymorphic sublimed unsolvated (Form 2) of para tertiary butyl calix[4]arene, said sublimed unsolvated para tertiary butyl calix[4]arene having the X-ray powder diffraction pattern as defined in Table 1, and further having monoclinic space group symmetry P1121/n with unit cell parameters a=12.675(5) Å, b=12.608(5) Å, c=25.687(10) Å, a=90o, b=90o, and g=90.273(8)o.

27. A process of preparing polymorphic sublimed unsolvated of para tertiary butyl calix[4]arene involving sublimation of para tertiary butyl calix[4]arene, in any degree of purity or as a solvate, to provide sublimed unsolvated of para tertiary butyl calix[4]arene.

28. A process of preparing polymorphic sublimed unsolvated of para tertiary butyl calix[4]arene involving raising the temperature of a solvate of para tertiary butyl calix[4]arene to a value sufficient to drive solvent molecules out of the solid para tertiary butyl calix[4]arene.

29. A composition of matter comprising a guest-host assembly having methane as the guest in sublimed unsolvated para tertiary butyl calix[4]arene.

30. A process for preparing a guest-host assembly having methane as the guest in sublimed unsolvated para tertiary butyl calix[4]arene comprising exposing sublimed unsolvated para tertiary butyl calix[4]arene to pressure in an atmosphere of methane.

31. A guest-host assembly having methane as the guest in sublimed unsolvated para tertiary butyl calix[4]arene used in a delivery method for methane as a fuel.

32. A guest-host assembly having hydrogen as the guest in sublimed unsolvated para tertiary butyl calix[4]arene used in a delivery method for hydrogen as a fuel.

* * * * *